Reissued Oct. 20, 1942

Re. 22,208

UNITED STATES PATENT OFFICE 22,208

COMPOSITION CAPABLE OF INHIBITING AGGLUTINATION OR HEMOLYSIS IN BLOOD

Ernest Witebsky and Niels C. Klendshoj, Buffalo, N. Y., assignors to The Buffalo Research Associates, Inc., Buffalo, N. Y., a corporation of New York No Drawing. Original No. 2,290,146, dated July 14, 1942, Serial No. 372,190, December 28, 1940. Application for reissue August 15, 1942, Serial No. 454,988. In Great Britain November 19, 1940

7 Claims. (Cl. 167—78)

This invention relates to compositions capable of inhibiting agglutination or hemolysis in blood.

At the turn of this century, Landsteiner discovered that the blood of all humans could be grouped into distinctly definite types depending upon the presence or absence of different characteristics. According to these characteristics, the red blood cells of humans are classified into the A and B structures. These A and B structures are readily determined by the use of substances, called isoagglutinins $\alpha$ and $\beta$ or the anti-A factor and the anti-B factor respectively, which are contained in human blood serum. Serum containing one of these isoagglutinins, when added to the red blood cell A and red blood cell B, each of which is in a separate container, agglutinates one cell structure but not the other to a degree depending upon the concentration of the isoagglutinins and the red blood cells. Thus, the anti-A factor in a serum agglutinates the A red blood corpuscles, but does not agglutinate the B red blood corpuscles. On the other hand, the anti-B factor in a serum agglutinates the B red blood corpuscles, but not the A red blood corpuscles.

In accordance with the discovery of Landsteiner, blood has been classified into four types known as the Landsteiner blood groups. These four groups, classified according to the International nomenclature, together with the structure in the cell and the isoagglutinins in the serum of each group, appear in the following table:

| Blood group or type | Structure in cells | Isoagglutinin in serum |
|---|---|---|
| O | | Anti-A+anti-B. |
| A | A | Anti-B. |
| B | B | Anti-A. |
| AB | A+B | |

It is observed that the blood corpuscles of the O type or group do not contain either the A or B properties, and consequently cannot be agglutinated and hemolyzed by the anti-B factor in the A type or the anti-A factor in the B type. Further, the anti-A and anti-B factors are absent in the AB type. Accordingly, it was recognized as much as thirty years ago that this O type blood, constituting about 40 to 45% of the population, might serve as universal blood suitable for transfusion. (Ottenberg, R.: J. Experimental Med. 13:425, 1911.) It was believed that blood of this type might be injected into any recipient without the risk of agglutination and hemolysis of the donor corpuscles. At that time the possibility of agglutination and hemolysis of donor corpuscles was considered a much more serious risk than the possibility of agglutination and hemolysis of the corpuscles of the recipient since the amount of blood injected was presumably substantially less than the total amount of blood present in the body of the recipient. In addition, the number of corpuscles present in the recipient which could attacked by isoagglutinins and hemolysins in the donor's blood was presumably substantially larger than the number of donor corpuscles injected.

The use of O type blood as a universal donor has been finally abandoned in many clinics as a result of a series of accidents, some of them resulting in death. These accidents are attributed not to the agglutination and hemolysis of O type corpuscles of the donor, but to agglutination and hemolysis of the corpuscles of the recipient since the type O blood serum may contain substantial amounts of both the anti-A and anti-B factors. In a careful review of the problem by Hesse in 1935, attention was drawn to the fact that there was a considerable percentage of O donors, the serum of which contains a sufficiently powerful anti-A isoagglutinin to permit of the serum being diluted from 32 to 64 times and still causing agglutination of type A corpuscles under conventional testing conditions. Similarly, a smaller percentage exhibited the same high capacity for agglutinating the B type corpuscles. Hesse reported a case in which dilution might be carried over 2000 to 1 and still the anti-A factor was capable of agglutinating the A type corpuscles. The conclusion drawn was that the type O blood could not therefore be safely employed as universal donor because even if the amount of blood injected were kept below the level of 100 to 200 cc. there could still be conditions under which the amount of isoagglutinins so introduced by the donor's blood serum would be sufficient to produce agglutination and hemolysis of the corpuscles of a recipient. Hesse pointed out that this risk would be greater in cases in which, such as hemorrhage or pronounced anemia, the blood volume or the number of red corpuscles had been substantially diminished. Since these are the cases in which transfusion is most frequently required, and since the reaction in question is mainly one of the number of corpuscles available and the amount of isoagglutinin introduced, the type O blood cannot safely be employed without any typing in all individuals unless steps are taken to inhibit the anti-A factor and the anti-B factor present in this blood prior to injection into the recipient.

In accordance with this invention, type O blood is rendered substantially safer for injection into any recipient by inhibiting in advance of such injection, both the anti-A factor and the anti-B factor present in the serum by adding to the O type blood an A specific substance and a B specific substance. The A specific substance is characterized by its ability to inactivate the anti-A factor in blood serum, while the B specific substance is characterized by its ability to inactivate the anti-B factor in blood serum. The A specific substance inactivates the anti-A factor present in O and B blood serum and the B specific substance inactivates the anti-B factor present in the O and A serum. These characteristics of both the A substance and B substance can be readily ascertained.

The A specific substance and the B specific substance may be added directly to the blood, which has been prevented from coagulation by the addition of an anticoagulating medium, such as sodium citrate. Alternately, the A specific substance and the B specific substance may be added to the solution of the anticoagulating medium prior to the addition of blood to that solution.

The A specific substance is determined by treating a serum which is known to contain the anti-A factor and subsequently adding A cells to the mixture. If no agglutination is discernible, the material contains the A substance. Likewise, the B specific substance can be determined by subjecting it to a serum known to contain the anti-B factor and subsequently adding B cells to the mixture. No agglutination appears upon the addition of the B cells to the mixture. This method of demonstrating the presence of the A specific substance and the B specific substance is known as the inhibition of agglutination. Accordingly, the presence or absence of the A specific substance or the B specific substance can readily be ascertained in a particular material by means of these tests.

Typical sources of the A specific substance are tissues and excretions of animals belonging to the blood group A and products derived from these animals, such a commercial peptones and pepsins. Typical sources of the B specific substance are the tissues and excretions of animals, including human beings, belonging to blood group B, such as saliva, gastric juices, urine, and gastrointestinal mucosa.

The presence of the A specific substance or the B specific substance can be determined by the method heretofore described. For example, saliva and gastric juices from animals belonging to the B group are tested by incubating at room temperature several samples containing descreasing amounts of the saliva and gastric juices (total volume 0.2 cc.) with 0.2 cc. of inactivated human serum containing the anti-B factor (dilution 1:3). After incubation, 0.2 cc. of a 1% suspension of human blood cells B are added to the mixture. Typical samples of the saliva and gastric juices gave the reaction appearing in the following table:

*Agglutination of human B cells by serum of group A after treatment of the latter with increasing dilutions of saliva and gastric juice of group B respectively*

| | Dilution of saliva and gastric juice respectively | Saliva | Gastric juice |
|---|---|---|---|
| 1 | 1:10 | − | − |
| 2 | 1:30 | − | − |
| 3 | 1:90 | − | − |
| 4 | 1:270 | − | − |
| 5 | 1:810 | − | − |
| 6 | 1:2430 | − | − |
| 7 | 1:7290 | + | ± |
| 8 | 1:21870 | + | + |
| 9 | 1:65610 | + | + |
| 10 | 1:196830 | ++ | ++ |
| 11 | 1:590490 | +++ | +++ |
| 12 | 0 | +++ | +++ |

−=no agglutination.
±=faint agglutination.
+=slight agglutination.
++=marked agglutination.
+++=strong agglutination.

The A specific substance may be isolated in relatively pure form from a material known to contain such substance, and the B specific substance can be isolated in relatively pure form safe for therapeutic use from a substance known to contain it. Essentially the same method can be employed for isolating A specific substance as that for isolating B specific substance from materials known to contain these substances. One general method for isolating A specific substance or B specific substance from materials known to contain either of these substances is as follows:

The specific substance is brought into solution in water, discarding any insoluble inert material which might be present; a crude fraction containing the active principle may be obtained from such solution by precipitation with a material in which the specific substance is insoluble, such as ethyl alcohol. Preferably the precipitation is conducted in the presence of an electrolyte, such as sodium acetate. From this crude fraction the specific substance may be redissolved in water and further purification may be obtained by repeating the described procedure a number of times, three times being a preferable number. At the end of these purification procedures, the active specific substance is contained in the clear water solution. This solution is subjected to any suitable deproteinizing process. It is preferable that this solution be adjusted to pH 4.8 by the use of a suitable buffer system. One deproteinizing process consists in repeatedly shaking the solution containing the specific substance with chloroform to which has been added a material which aids in preventing formation of a stable emulsion. Butyl alcohol or amyl alcohol may be mentioned as suitable materials for this purpose. The shaking is continued until a sample of the clear supernatant liquid does not manifest any reaction of protein when subjected to such commonly known reagents as sulfosalicylic acid and saturation with picric acid. The deproteinized supernatant liquid is subsequently dialyzed through any suitable membrane, such as Cellophane, to remove smaller molecules and ions present, such as might be derived from the buffer system used. At the end of dialysis the active specific substance is obtained as a precipitate by adding the solution to an amount of acetone sufficient to cause complete precipitation of the active principle. Ten volumes of acetone have been found to be sufficient for practical purposes. An intermediate step, comprising another precipitation with 2½ volumes of ethyl alcohol, may precede the acetone precipitation if deemed necessary. The precipitate is washed several times with acetone, and finally dried. It is preferable to perform the drying of the active principle in vacuum in the presence of one of the commonly employed dehydrating agents, such as calcium chloride or sulphuric acid. The A specific substance or the B specific substance prepared in accordance with this method is substantially free of proteins.

Typical examples of the preparation of the A specific substance and the B specific substance are as follows:

EXAMPLE 1.—*Preparation of A specific substance*

450 g. of peptone known to contain the A specific substance and 180 g. of crystalline sodium acetate are dissolved in 1350 cc. of water and the crude fraction containing the A specific substance is precipitated by the addition of 3375 cc. of 95% ethyl alcohol. The precipitate is collected in centrifuge tubes after a period of 24 hours. 270 cc. of water are added to this precipitate and the mixture is centrifuged. Any undissolved sediment is discarded. The solution contains the A specific substance and to this solution are added 45 grams of crystalline sodium acetate and 675 cc. of ethyl alcohol. The mixture is permitted to stand for a period of approximately 24 hours and centrifuged. The precipitate which formed is dissolved in 150 cc. of water, centrifuged, and any undissolved sediment discarded. To the solution are added 24 grams of crystalline sodium acetate and 2½ volumes of 95% ethyl alcohol. The mixture is permitted to stand over night and centrifuged. To the precipitate, which contains the A specific substance, are added 180 cc. of water. The mixture is centrifuged and any undissolved sediment discarded. To the solution are added 27 grams of crystalline sodium acetate, and the pH of the solution adjusted to 4.8 by the addition of 20% acetic acid. This solution is deproteinized by shaking with a mixture of 40 cc. of chloroform and 8 cc. of butyl alcohol for a period of approximately 16 hours. The water phase contains the A specific substance and this water solution is separated from the chloroform and butyl alcohol phase. The resulting water solution is tested for protein with 20% trichloracetic acid, 5% sulfosalicylic acid, or saturation with picric acid. The deproteinizing procedure is repeated until a negative test is obtained. The A specific substance is recovered from this solution by precipitation with 2½ volumes of 95% ethyl alcohol. The precipitate which is formed is dissolved in water and dialyzed through Cellophane against successive changes of distilled water. The solutions are kept in a refrigerator at a temperature of approximately 5° C. during the dialysis. The A specific substance is finally precipitated by the addition of approximately 10 volumes of acetone. The A specific substance tends to remain in colloidal suspension, but forms a flocculent precipitate quite readily after the addition of a few crystals of sodium chloride. The precipitate which comprises the A specific substance is collected on a hardened filter paper, washed with acetone and dried over sulphuric acid.

EXAMPLE 2.—*Preparation of the B specific substance*

110 cc. of gastric juices from patients belonging to group B and which contain the B specific substance, as determined by the tests heretofore described, are centrifuged and the supernatant fluid is heated for five minutes in a boiling water bath. After cooling the material is again centrifuged and 14 grams of anhydrous sodium acetate are dissolved in the clear supernatant fluid. 275 cc. of 95% ethyl alcohol are then added to the mixture and the mixture is permitted to stand for a period of 24 hours. It is then centrifuged, and to the resulting precipitate, which contains the B specific substance are added 10 cc. of normal physiological saline solution, and after approximately 24 hours the mixture is again centrifuged and any undissolved sediment is discarded. 1.4 grams of anhydrous sodium acetate followed by 25 cc. of alcohol are added to the supernatant fluid and the mixture allowed to stand approximately 24 hours. A precipitate forms which contains the B specific substance and this precipitate is removed by centrifugation. This precipitate is again treated with approximately 10 cc. of normal physiological saline solution and permitted to stand for a period of approximately 24 hours. It is then centrifuged and any undissolved sediment discarded. 1.4 grams of anhydrous sodium acetate and 25 cc. of 95% ethyl alcohol are added to the solution and the mixture permitted to stand for approximately 24 hours. The precipitate which forms is separated by centrifugation and dissolved in about 10 cc. of water. Any insoluble material which remains undissolved after a period of 24 hours is discarded. The solution is adjusted to a pH of 4.8 employing sodium acetate and acetic acid. The solution is deproteinized by shaking for approximately 16 hours with a mixture of 10 cc. of chloroform and 2 cc. of butyl alcohol. The resulting solution is tested for protein with 20% trichloracetic acid, 5% sulfosalicylic acid, or saturation with picric acid. The deproteinizing procedure is repeated until a negative test is obtained. The water phase, after treatment with chloroform and butyl alcohol, contains the B specific substance and this water solution is dialyzed against successive changes of distilled water until substantially free from electrolytes. The dialysis is performed at a temperature of approximately 5° C. The dialysate is subsequently evaporated in vacuo to a volume of approximately 3.5 cc. To this solution are added 35 cc. of acetone. A few crystals of sodium chloride are added to facilitate the separation of the precipitate. The precipitate is collected in a centrifuge tube, washed with acetone and dried over calcium chloride in vacuo. The resulting product comprises the B specific substance. A 1% solution of this material gives a strong positive Molisch test. No precipitate is obtained with trichloracetic acid, sulfosalicylic acid, or a saturated solution of picric acid.

Desirably the potency of the A specific substance and the B specific substance can be determined by the following methods:

For determining the potency of the A specific substance, the titer of the anti-A factor of a serum belonging to group B or group O is first ascertained. Preferably this titer is from 1:16 to 1:128. The titer is defined as the greatest dilution of a serum at which discernible agglutination occurs when mixed with red cells of group A. It is ascertained readily by taking varying dilutions.

e. g., 1:2, 1:4, 1:8, etc., of the serum of group B or group O and mixing these dilutions with equal volumes of a washed A cell suspension (about 1%). The greatest dilution at which agglutination is discernible is called the titer.

1 milligram of the A specific substance dissolved in 1 cc. of physiological saline solution is added to 10 cc. of serum of group B or group O containing the anti-A factor, the titer of which has been determined as heretofore described. After incubating this mixture at room temperature for 15 minutes, the titer of the treated serum is determined by preparing dilutions, e. g., 1:2, 1:4, 1:8, etc., and adding equal volumes of a 1% A cell suspension to these various dilutions. 1 milligram of the A specific substance prepared in accordance with the method described in Example 1 reduces the titer of the anti-A factor in 10 cc. of serum to at least one fourth of the titer of the untreated serum.

The potency of the B specific substance is determined in a like manner, except that serum of group A or group O containing the anti-B factor is used. 1 milligram of the B specific substance prepared in accordance with the method described in Example 2 reduces the titer of the anti-B factor in 10 cc. of group B or group O serum to at least one fourth the titer of the untreated serum. 1 milligram of the A specific substance and 1 milligram of the B specific substance prepared in accordance with the methods described in Examples 1 and 2 reduce the anti-A and anti-B factors in 10 cc. of serum of group O at least to one fourth of that of the untreated serum. This fact can be ascertained by testing the serum of group O by the methods heretofore described.

For the utilization of the A specific substance and the B specific substance in rendering substantially inactive the anti-A factor and the anti-B factor in O type blood, the A specific substance and the B specific substance are added to either the O type blood containing an anticoagulating medium, such as sodium citrate, or the A specific substance and the B specific substance may be added to the solution of the anticoagulating medium before the blood has been added thereto. The minimum amount of the A specific substance and the B specific substance required for neutralization of the anti-A factor and anti-B factor can be ascertained by titer determination. For practical purposes, 25 milligrams of the A specific substance prepared in accordance with the method outlined in Example 1 and 10 milligrams of the B specific substance prepared in accordance with the method outlined in Example 2 have been found satisfactory to render inactive the anti-A and the anti-B factors in 500 cc. of most O blood.

A solution of the A specific substance and the B specific substance may be prepared for utilization in blood transfusion work. For example, 25 milligrams of the A specific substance and 10 milligrams of the B specific substance may be dissolved in 70 cc. of a solution containing 2½% sodium citrate U. S. P. and 0.85% sodium chloride C. P. This solution is suitable for the purpose of mixing with 500 cc. of universal O blood to prevent coagulation and produce the reduction in isoagglutinin titer as previously described. A practical way of performing this procedure would be to mix 25 milligrams of the A specific substance with 10 milligrams of the B specific substance and dissolve this mixture under sterile precautions in physiological saline solution just prior to the addition to O type blood containing an anticoagulating agent, such as potassium oxalate, heparin and hirudine. The specific substances could also be contained in individual vials and dissolved, prepared individually before the injection into the blood. However, it is preferred to prepare a solution of the A specific substance and the B specific substance prior to the addition of these substances to the O type blood.

The A specific substance and the B specific substance may likewise be employed to render substantially ineffective the isoagglutinins present in O type serum or plasma or other derivative of the O type blood. For example, 25 milligrams of the A specific substance, prepared in accordance with the method outlined in Example 1, and 10 milligrams of the B specific substance, prepared in accordance with the method outlined in Example 2, may be added to 250 cc. of serum obtained from O type blood. In all cases, whether it be whole O type blood, or serum or plasma derived from O type blood, the A and B specific substances render substantially ineffective the isoagglutinins originally present—the anti-A factor and the anti-B factor—so that such treated whole blood or serum does not cause any appreciable degree of agglutination or hemolysis with the red cells or corpuscles of the recipient regardless of the blood group of the recipient.

The red corpuscles known as the AB corpuscles from the blood group AB are agglutinated by the anti-A factor or the anti-B factor. The A specific substance inhibits the agglutination of the AB corpuscles as well as the A corpuscles when added to blood or a derivative of blood containing the anti-A factor, such as contained in O or B blood group, while the B specific substance inhibits the agglutination of the AB corpuscles as well as the B corpuscles when added to blood or a derivative of blood from O or A blood group. Accordingly, these substances may be utilized for rendering blood or a derivative of blood of blood group A or blood group B suitable for use in transfusion to patients of the AB blood group. For example, the B specific substance may be added to A blood containing the anti-B factor. Such treated A blood would be satisfactory for transfusion to patients belonging to the AB group. Likewise, blood or a derivative of blood belonging to blood group B could be rendered safe for transfusion to patients of the AB group by adding thereto a quantity of the A specific substance sufficient to render ineffective the anti-A factor in the B blood or derivative of B blood. If it is desired to employ O blood or a derivative of O blood for transfusion in patients belonging to blood group AB, it is necessary to add both the A and B specific substances to the O blood or derivative of O blood as heretofore described, since the O blood or derivative thereof contains both the anti-A and anti-B factors.

What is claimed is:

1. In combination, A specific substance capable of inhibiting the agglutination of the A corpuscles of A type blood by the anti-A factor of untreated B type serum and B specific substance capable of inhibiting the agglutination of the B corpuscles of B type blood by the anti-B factor of untreated A type serum.

2. In combination, A specific substance capable of inhibiting the agglutination of the A corpuscles of A type blood by the anti-A factor of untreated B type serum and B specific substance capable of inhibiting the agglutination of the B corpuscles of B type blood by the anti-B factor of untreated A type serum, said A specific substance and said B specific substance being substantially free of proteins.

3. In combination, A specific substance, 1 milligram of which is capable of reducing the activity of the anti-A factor in 10 cc. of untreated B type serum to at least one fourth of the prior activity of said anti-A factor; and B specific substance, 1 milligram of which is capable of reducing the activity of the anti-B factor in 10 cc. of untreated A type serum to a least one fourth of the prior activity of said anti-B factor.

4. The method of conditioning a member selected from the class consisting of O type blood and derivatives of O type blood suitable for transfusion which comprises reacting the isoagglutinins in O type blood with A specific substance capable of inhibiting the agglutination of the A corpuscles of A type blood by the anti-A factor of untreated B type serum, and B specific substance capable of inhibiting the agglutination of the B corpuscles of B type blood by the anti-B factor of untreated A type serum.

5. In combination, A specific substance capable of inhibiting the agglutination of the A corpuscles of A type blood by the anti-A factor of untreated B type serum, B specific substance capable of inhibiting the agglutination of the B corpuscles of B type blood by the anti-B factor of untreated A type serum and a member selected from the class which consists of whole O type blood and derivatives of O type blood.

6. A solution of A specific substance capable of inhibiting the agglutination of the A corpuscles of A type blood by the anti-A factor of untreated B type serum, and B specific substance capable of inhibiting the agglutination of B corpuscles of B type blood by the anti-B factor of untreated A type serum, said solution containing an anticoagulating agent.

7. A solution of A specific substance capable of inhibiting the agglutination of the A corpuscles of A type blood by the anti-A factor of untreated B type serum, and B specific substance capable of inhibiting the agglutination of B corpuscles of B type blood by the anti-B factor of untreated A type serum, said solution containing sodium citrate and sodium chloride.

ERNEST WITEBSKY.
NIELS C. KLENDSHOJ.